(12) United States Patent
Minami et al.

(10) Patent No.: US 10,743,831 B2
(45) Date of Patent: Aug. 18, 2020

(54) RADIATION IMAGE PROCESSING DEVICE

(71) Applicant: Konica Minolta, Inc., Tokyo (JP)

(72) Inventors: Hirotake Minami, Fuchu (JP); Tatsuya Takagi, Mitaka (JP)

(73) Assignee: KONICA MINOLTA, INC., Tokyo (JP)

( * ) Notice: Subject to any disclaimer, the term of this patent is extended or adjusted under 35 U.S.C. 154(b) by 219 days.

(21) Appl. No.: 15/916,941

(22) Filed: Mar. 9, 2018

(65) Prior Publication Data

US 2018/0263584 A1    Sep. 20, 2018

(30) Foreign Application Priority Data

Mar. 14, 2017    (JP) ................... 2017-048577

(51) Int. Cl.
 *G06K 9/00*    (2006.01)
 *A61B 6/00*    (2006.01)
 (Continued)

(52) U.S. Cl.
 CPC ............. *A61B 6/527* (2013.01); *A61B 6/50* (2013.01); *A61B 6/5264* (2013.01); *G06T 5/008* (2013.01);
 (Continued)

(58) Field of Classification Search
 CPC ......... A61B 6/462; A61B 6/50; A61B 6/5264; A61B 6/527; G06T 2207/10016;
 (Continued)

(56) References Cited

U.S. PATENT DOCUMENTS 5,982,915 A  * 11/1999 Doi ..................... G06T 3/0081
                                                       382/130
2005/0111719 A1*  5/2005 Pescatore .............. G06T 3/0068
                                                       382/130
(Continued)

FOREIGN PATENT DOCUMENTS

JP        2006-263224 A     10/2006
JP        2010268979 A      12/2010
(Continued)

OTHER PUBLICATIONS

JPO, Office Action for the corresponding Japanese patent application No. 2017-048577, dated Jun. 2, 2020, with English translation.

*Primary Examiner* — Ian L Lemieux
(74) *Attorney, Agent, or Firm* — Lucas & Mercanti, LLP

(57) ABSTRACT

A radiation image processing device which performs image processing to a moving image that is obtained by emitting radiation to a subject, the radiation image processing device including a hardware processor that: extracts a reference region from each of a plurality of frame images which form the moving image; calculates an image processing condition of the reference region for each of the frame images from which the reference region is extracted; determines a standard image processing condition which is a standard based on the calculated image processing condition of each of the frame images; and performs image processing by applying the determined standard image processing condition to each of the frame images.

8 Claims, 3 Drawing Sheets

(51) Int. Cl.
*G06T 7/00* (2017.01)
*G06T 5/50* (2006.01)
*G06T 5/00* (2006.01)

(52) U.S. Cl.
CPC .............. *G06T 5/50* (2013.01); *G06T 7/0012* (2013.01); *A61B 6/462* (2013.01); *G06T 2207/10016* (2013.01); *G06T 2207/10116* (2013.01); *G06T 2207/20021* (2013.01); *G06T 2207/30061* (2013.01)

(58) Field of Classification Search
CPC . G06T 2207/10116; G06T 2207/20021; G06T 2207/30061; G06T 5/008; G06T 5/50; G06T 7/0012
See application file for complete search history.

(56) References Cited

U.S. PATENT DOCUMENTS

| | | | | |
|---|---|---|---|---|
| 2005/0207630 A1* | 9/2005 | Chan | ........................ | A61B 6/466 |
| | | | | 382/131 |
| 2007/0263929 A1* | 11/2007 | Kaji | ........................ | A61B 6/00 |
| | | | | 382/168 |
| 2008/0118139 A1* | 5/2008 | Huo | ........................ | G06T 5/009 |
| | | | | 382/132 |
| 2008/0317317 A1* | 12/2008 | Shekhar | ................ | G06T 3/0081 |
| | | | | 382/131 |
| 2008/0317322 A1* | 12/2008 | Acharyya | ............. | G06T 7/0012 |
| | | | | 382/132 |

FOREIGN PATENT DOCUMENTS

| | | |
|---|---|---|
| JP | 2011005050 A | 1/2011 |
| JP | 2016-214725 A | 12/2016 |

\* cited by examiner

*FIG.3A*
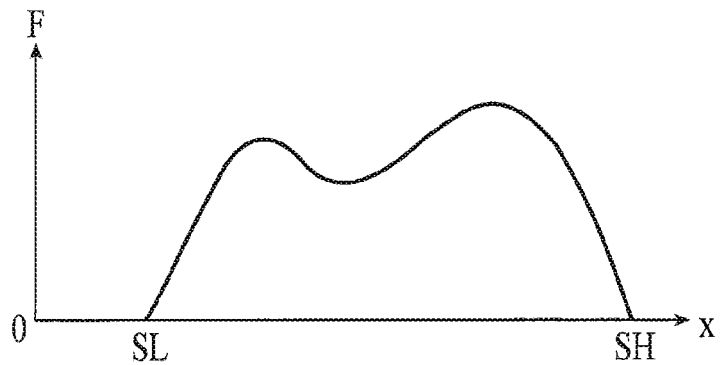
*FIG.3B*
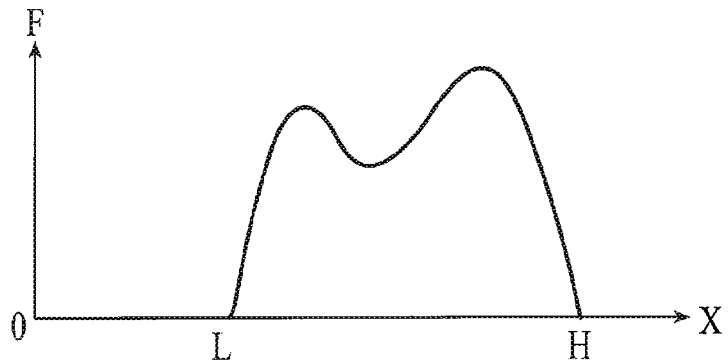
*FIG.4*
| No. | 1 | 2 | 3 | 4 | 5 | 6 | 7 |
|---|---|---|---|---|---|---|---|
| G VALUE | 825 | 824 | 827 | 822 | 831 | 830 | 839 |
| S VALUE | 1483 | 1489 | 1485 | 1481 | 1475 | 1478 | 1464 |
*FIG.5A*
| No. | 3 | 1 | 2 | 6 | 5 | 4 | 7 |
|---|---|---|---|---|---|---|---|
| ΔGn | 0 | 2 | 3 | 3 | 4 | 5 | 12 |
*FIG.5B*
| No. | 4 | 1 | 6 | 3 | 5 | 2 | 7 |
|---|---|---|---|---|---|---|---|
| ΔSn | 0 | 2 | 3 | 4 | 6 | 8 | 17 |

RADIATION IMAGE PROCESSING DEVICE

CROSS-REFERENCE TO RELATED APPLICATIONS

The entire disclosure of Japanese Patent Application No. 2017-048577 filed on Mar. 14, 2017 is incorporated herein by reference in its entirety.

BACKGROUND

1. Technological Field

The present invention relates to a radiation image processing device, and especially relates to a radiation image processing device which performs image processing to a moving image that is obtained by emitting radiation to a subject.

2. Description of the Related Art

In the field of radiation imaging, conventional CR (Computed Radiography) devices using films/screens or stimulable phosphor plates can take only still images of subjects. However, when semiconductor image sensors such as FPDs (flat panel detectors) are used, it is possible to obtain moving images at imaging sites such as thoraxes of subjects since the obtained radiation images can be stored in storage sections in the devices or can be transmitted to external devices.

In recent years, attempts have been made to use the obtained moving images for diagnosis (for example, see Japanese Patent Application Laid-Open Publication No. 2010-268979). There have also been developed radiation image processing devices which perform image processing so as to utilize the moving images for diagnosis.

For example, when a moving image of lung regions of a patient who is a subject is obtained, frame images at respective times T ($T=t_0$ to $t_6$) of the lung regions r can be obtained as shown in FIG. 6, for example. Since the size, the position, the density (that is, the signal value of each pixel) and such like of the lung regions r change temporally, it is possible to determine the maximum inspiratory position, the maximum expiratory position, the expiratory period, the inspiratory period and such like of the lung regions r and obtain information which can be used for diagnosis of lung functions (the ventilation function, the pulmonary blood flow function and such like) by analyzing the temporal changes of the size, the position, the density and such like.

As a method for performing image processing to a moving image by a radiation image processing device, for example, Japanese Patent Application Laid-Open Publication No. 2011-5050 describes extracting a reference region which is a reference of an image by an image processing device which performs tone conversion of the image that was obtained in a radiation imaging system, and when the image changes, performing tone conversion so as to suppress the variation in the contrast caused by the change in the image for the extracted reference region, performing tone conversion so as to reflect the variation in the contrast for the other region, and thereby performing image processing so as to make the contrast variation stable between the frames of the moving image.

In a case where a moving image is used for diagnosis or the like as described above, it is desirable that the lung regions r are accurately photographed at a high density corresponding to the amount of inhaled air when a patient inhales air into the lungs as shown in FIG. 6 for example, and the lung regions r are accurately photographed at a low density by the amount of the exhaled air when the patient exhales air from the lungs. By accurately changing the contrast (that is, the density) of the lung regions r during reproduction of the moving image, the doctor can easily find abnormalities of the shape, the movement and such like of the lung regions r, abnormalities of the ventilation function and the pulmonary blood flow function and such like when the patient breathes.

However, in a case of performing image processing as described in Japanese Patent Application Laid-Open Publication No. 2011-5050, the variation in the contrast caused by the change in the image is suppressed when the reference region is the lung regions r, for example. Thus, since the variation in the contrast of the lung regions r caused by the breathing of the patient is suppressed contrary to the above case, it is possibly difficult to find the above-mentioned abnormalities of the shape, the movement and such like of the lung regions r, the abnormalities of the ventilation function and the pulmonary function and such like when the patient breathes.

In addition, when image processing such as contrast adjustment is performed for each of the frame images forming the moving image, the contrast is not uniform between the frame images. Thus, the moving image is possibly difficult to see when the moving image is reproduced. The brightness and such like of the imaging site such as the lung regions r or the entire image also possibly changes between the frame images, for example. Thus, it is difficult to distinguish whether the change in the brightness at the imaging site or the like is caused by the image processing for each of the frame images or caused by existence of a lesion, which possibly influences the diagnosis by the doctor.

SUMMARY

The present invention has been made in consideration of the above problems, and an object of the present invention is to provide a radiation image processing device which can perform contrast adjustment of each frame image on the basis of a uniform standard when performing image processing to each frame image forming the moving image and which can generate a moving image enabling a doctor to accurately grasp the shape, the movement, the density change and such like at the imaging site when the doctor watch the moving image.

To achieve at least one of the abovementioned objects, according to an aspect of the present invention, a radiation image processing device reflecting one aspect of the present invention includes performs image processing to a moving image that is obtained by emitting radiation to a subject, the radiation image processing device including a hardware processor that: extracts a reference region from each of a plurality of frame images which form the moving image; calculates an image processing condition of the reference region for each of the frame images from which the reference region is extracted; determines a standard image processing condition which is a standard based on the calculated image processing condition of each of the frame images; and performs image processing by applying the determined standard image processing condition to each of the frame images.

BRIEF DESCRIPTION OF THE DRAWINGS

The advantages and features provided by one or more embodiments of the invention will become more fully understood from the detailed description given hereinafter and the appended drawings which are given by way of illustration only, and thus are not intended as a definition of the limits of the present invention, and wherein:

FIG. 3A is a histogram showing distribution of signal values in a frame image;

FIG. 3B is a histogram showing distribution of normalized signal values;

FIG. 4 is a diagram showing an example of G values and S values which are calculated for respective frame images;

FIG. 5A is a diagram arranging the differences between the G values of the respective frame images in the case of FIG. 4 and the median value in order of increasing the differences;

FIG. 5B is a diagram arranging the differences between the S values of the respective frame images in the case of FIG. 4 and the median value in order of increasing the differences.

DETAILED DESCRIPTION OF THE EMBODIMENTS

Hereinafter, one or more embodiments of a radiation image processing device according to the present invention will be described with reference to the drawings. However, the scope of the invention is not limited to the disclosed embodiments or illustrated examples.

Figure 1:
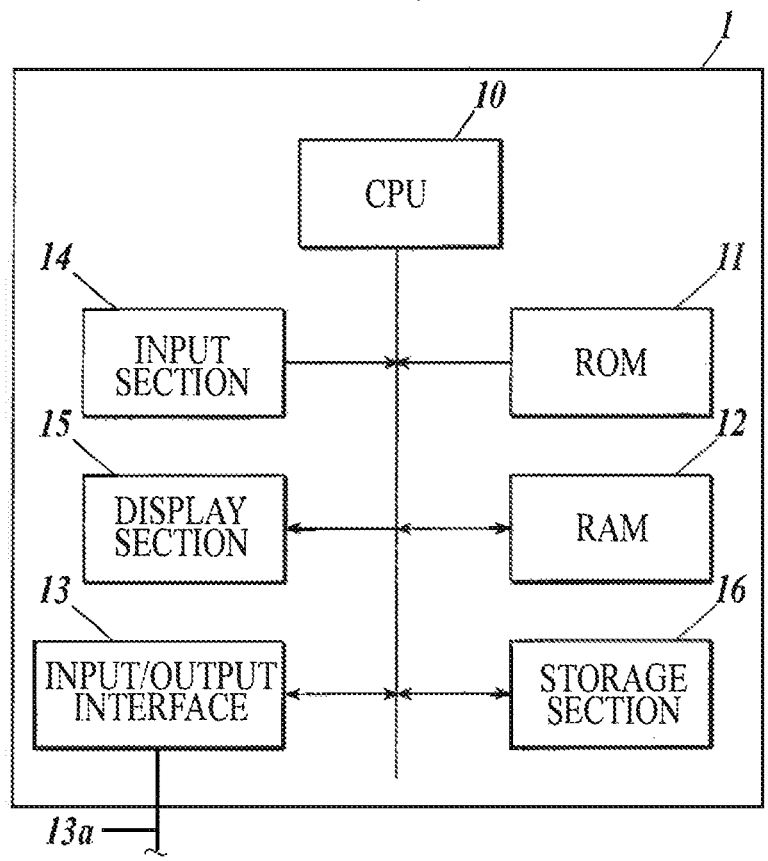
FIG. 1 is a block diagram showing the configuration of a radiation image processing device in an embodiment.

The configuration of a radiation image processing device 1 in an embodiment will be described. FIG. 1 is a block diagram showing the configuration of the radiation image processing device 1 in the embodiment. In the embodiment, as shown in FIG. 1, the radiation image processing device 1 is configured by including a general purpose computer in which a CPU (Central Processing Unit) 10, a ROM (Read Only Memory) 11, a RAM (Random Access Memory) 12, an input/output interface 13 and such like are connected to a bus. The radiation image processing device 1 is connected 13a to other devices or systems not shown in the drawings via the input/output interface 13, a communication network not shown in the drawings or the like.

The CPU 10 is also connected to an input section 14 which is configured by including a keyboard, a mouse and a touch panel, a display section 15 which is configured by including a CRT (Cathode Ray Tube) and an LCD (Liquid Crystal Display) and such like. The CPU 10 is also connected to a storage section 16 which is configured by including a non-volatile semiconductor memory, an HDD (Hard Disk Drive) and such like.

The radiation image processing device 1 may be configured as a dedicated device, not as the above-mentioned general purpose computer. In the embodiment, the CPU 10 is configured to function as a reference region extraction section, an image processing condition calculation section, a standard image processing condition determination section and an image processing section according to the present invention as described later. Thus, hereinafter, the CPU 10 is described as the reference region extraction section 10, for example. However, any of the above sections may be configured by separate unit(s) or module(s) different from the CPU 10, for example.

Though the radiation image processing device 1 may be configured as a single device as shown in FIG. 1, any of the above sections may be configured as separate device(s), for example. The radiation image processing device 1 is not limited to the case shown in FIG. 1 (that is, the case of configuring the radiation image processing device 1 as a single device). Furthermore, though not shown in the drawings, the radiation image processing device 1 may be integrally configured with an imaging device which takes a moving image, a control device which controls taking of the moving image, an image analysis device which analyzes the obtained moving image, a storage device which stores the obtained moving image or the like.

In the embodiment, the radiation image processing device 1 performs image processing to the moving image which was obtained by emitting radiation to a patient who is a subject from a radiation emission device not shown in the drawings. The reference region extraction section 10 extracts a reference region from each of the plurality of frame images forming the moving image. The image processing condition calculation section 10 calculates an optimum image processing condition of the reference region for each of the frame images from which the reference region extraction section 10 extracted the reference region.

The standard image processing condition determination section 10 determines a standard image processing condition which is a standard on the basis of the image processing condition of each of the frame images which was calculated by the image processing condition calculation section 10. The image processing section 10 performs image processing by applying the standard image processing condition which was determined by the standard image processing condition determination section 10 to each of the frame images.

Hereinafter, specific description will be made. The action of the radiation image processing device 1 according to the embodiment will be described together. Hereinafter, the description will be made by taking, as an example, a case where the image processing condition includes two parameters of a G value and a S value which are used in normalization processing including contrast adjustment to each of the frame images forming the moving image.

Here, the G value represents a gradient. The G value represents a gradient adjustment amount (Window Width: WW) in the normalization processing before applying an LUT (Look Up Table) to the signal value of each pixel in the frame images, and thus, the G value is used when the contrast is adjusted. The S value represents a shift amount in the normalization processing, and thus, the S value is a value for adjusting the density of the entire image (Window Level: WL).

Figure 6:
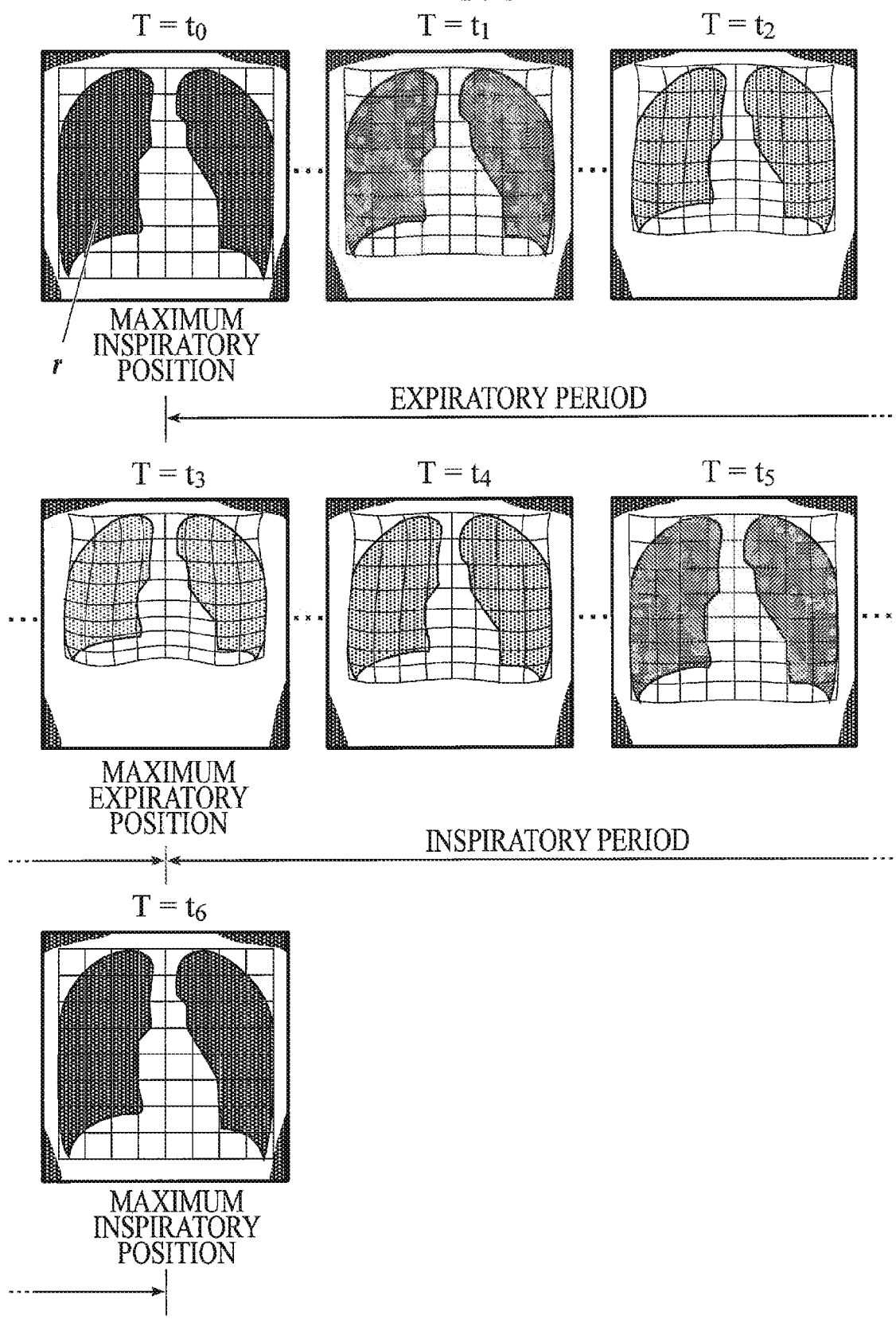
FIG. 6 is a view showing an example of the frame images which are taken when a moving image of lung regions is obtained.

The present invention can also be applied to cases where the parameter of the image processing condition is other than the above G value and the S value. The image processing in those cases are also performed in a manner similar to the manner described below. Though the description below is made for a case of taking a moving image (see FIG. 6) of a thorax including the lung regions r of the subject, the present invention is not limited to this case.

[Reference Region Extraction Processing]

Figure 2:
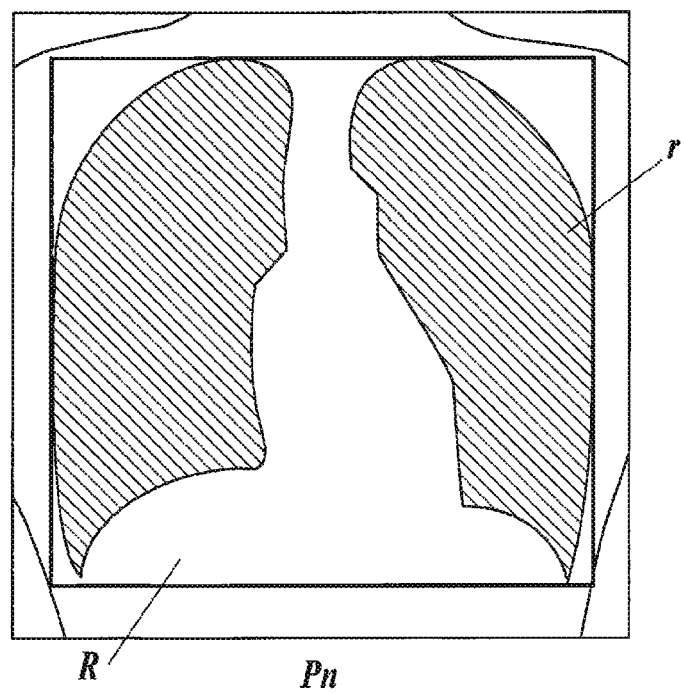
FIG. 2 is a view showing an example of a reference region which is extracted from a frame image Pn.

First, the reference region extraction section 10 of the radiation image processing device 1 obtains data (that is, the signal value of each pixel) for a plurality of frame images Pn forming a moving image from an imaging device (not shown in the drawings) which obtained the moving image, the storage device which stores the obtained moving image, or the like. The reference region extraction section 10 extracts a reference region R from each of the frame images Pn as shown in FIG. 2 for each of the frame images Pn. FIG. 2 illustrates a case where the reference region extraction section 10 extracts lung regions r which are a target of imaging by analyzing the frame image Pn and sets the rectangular region including the lung regions r as the reference region R.

In this case, the reference region extraction section 10 may be configured to extract the reference region R from each of all the frame images Pn forming the moving image. However, for example, the reference region extraction section 10 may be configured to extract the reference region R from each of a plurality of frame images Pn among all the frame images Pn, the plurality of frame images Pn being selected from the moving image by the user such as a radiation technologist and a doctor.

By the former configuration, it is possible to appropriately determine the standard image processing condition by the after-mentioned standard image processing condition determination section 10 with all the frame images Pn forming the moving image as the target. By the latter configuration, the number of frame images Pn which are targeted by the after-mentioned image processing condition calculation section 10 and the standard image processing condition determination section 10 decreases. Thus, it is possible to shorten the time required for each processing by each of the sections by the decreased amount. Furthermore, the after-mentioned standard image processing condition determination section 10 determines the standard image processing condition by targeting each of the frame images Pn which the user such as a radiation technologist and a doctor desires to especially focus on. Thus, it is possible to appropriately determine the standard image processing condition corresponding to the intention of the user such as a radiation technologist and a doctor.

[Image Processing Condition Calculation Processing]

The image processing condition calculation section 10 calculates an optimum image processing condition (that is, the G value and the S value in this case) of the reference region R for each of the frame images Pn from which the reference region extraction section 10 extracted the reference region R (that is, for each of the above mentioned all the frame images Pn or the plurality of frame images Pn among all the frame images Pn).

Here, normalization processing to the frame image Pn (that is, one image Pn) will be briefly described. In the normalization processing, in a case where the signal values x are distributed as shown in FIG. 3A (the vertical axis is the frequency F), for example, the signal values x are converted into the normalized signal values X in accordance with the following expression (1) so that the highest value SH and the lowest value SL of the signal values x are respectively the highest value H and the lowest value L which are determined in advance as shown in FIG. 3B, for example. The constants G and S at this time are the above G value and the S value.

$$X = G \times x + S \quad (1)$$

Since the above relationship leads to $H = G \times SH + S$ and $L = G \times SL + S$, the G value and the S value are calculated in the following expressions.

$$G = (H-L)/(SH-SL) \quad (2)$$

$$S = (L \times SH - H \times SL)/(SH-SL) \quad (3)$$

[Standard Image Processing Condition Determination Processing]

The standard image processing condition determination section 10 determines the standard image processing condition ($G_{st}$, $S_{st}$) which is a standard on the basis of the image processing condition, that is, the G value and the S value for each of the frame images Pn (all the frame images Pn or the plurality of frame images Pn among all the frame images Pn) which were calculated by the image processing condition calculation section 10 as described above.

At that time, in the embodiment, the standard image processing condition determination section 10 selects one frame image Pn from the plurality of frame images Pn for each of which the image processing condition calculation section 10 calculated the image processing condition (the G value and the S value), and determines the image processing condition (G value and S value) of the selected one frame image Pn as the standard image processing condition ($G_{st}$ and $S_{st}$).

As the method for selecting one frame image Pn from among the plurality of frame images Pn for each of which the image processing condition calculation section 10 calculated the image processing condition (here, simply referred to as the plurality of frame images Pn), for example, a histogram may be applied to each of the calculated G values and the S values of the plurality of frame images Pn to select the frame image Pn for which the G value and the S value have smallest shifts from the respective median values (or average values. the same applies hereinafter), for example.

That is, in order to simplify the explanation, the description will be made by taking, as an example, a case where the moving image is formed of seven frame images Pn (that is, P1 to P7), and the image processing condition calculation section 10 calculates the G values and the S values for all the frame images P1 to P7 as a target as shown in FIG. 4, for example. In this case, the median value of the G value is 827 of the image No. 3 (frame image P3), and the median value of the S value is 1481 of the image No. 4 (frame image P4).

For example, the difference $\Delta Gn$ and $\Delta Sn$ between the G value and the S value of each of the frame images Pn and the respective median values are defined and calculated as in the following expressions (4) and (5). When the calculated $\Delta Gns$ and $\Delta Sns$ are arranged in increasing order of the respective $\Delta Gns$ and $\Delta Sns$, the results are obtained as shown in FIGS. 5A and 5B.

$$\Delta Gn = |(\text{median value of } G \text{ value}) - (G \text{ value of frame image } Pn)| \quad (4)$$

$$\Delta Sn = |(\text{median value of } S \text{ value}) - (S \text{ value of frame image } Pn)| \quad (5)$$

For example, the standard image processing condition determination section 10 may calculate the distance Ln which is defined in the following expression (6), and determine, as the standard image processing conditions $G_{st}$ and $S_{st}$ which is a standard, the image processing condition, that is, the G value and the S value in the frame image Pn which has the smallest distance Ln. In the case shown in FIG. 4, the image processing condition, that is, the G value and the S value of the frame image P are determined as the standard image processing condition $G_{st}$ and $S_{st}$ which is a standard.

$$L = (\Delta Gn^2 + \Delta Sn^2)^{1/2} \quad (6)$$

There is possibly a case where any of the G value and the S value which were calculated for each of the frame images Pn by the image processing condition calculation section 10 in the above image processing condition calculation processing is a value calculated by wrong processing (hereinafter, referred to as the outlier value). Between the G value and the S value, it is the S value that more largely influences the image processing when the outlier value is adopted.

Thus, the frame image Pn for which the S value is the outlier value may be preferentially excluded from the target of the standard image processing condition determination processing. In this case, for example, the frame image Pn which has large differences ΔGn and ΔSn between the G value and the S value and the respective median values calculated in the above expressions (4) and (5) may be determined as the frame image Pn for which the G value and the S value are outlier values.

When the above is described for, as an example, a case shown in FIG. 4, the standard image processing condition determination section 10 calculates the differences ΔGn and ΔSn between the G value and the S value and the respective median values for each of the frame images Pn in accordance with the above expressions (4) and (5) on the basis of the distribution of FIG. 4 similarly to the above case (see FIGS. 5A and 5B). Then, the standard image processing condition determination section 10 first excludes the frame image Pn for which the G value is the outlier value from the target of the standard image processing condition determination processing.

At that time, as described above, since the S value has priority over the G value, it is desirable that the frame images Pn which are excluded at this point (that is, the frame images Pn for which the G value is the outlier value) are half of the entire frame images or less at the most. When two frame images Pn are excluded at this point, from the result shown in FIG. 5A, the frame image P7 having the largest difference ΔGn and the frame image P4 having the second largest difference ΔGn are excluded in this case.

Thereafter, the difference ΔSn is focused on, and the frame image Pn having the smallest difference ΔSn is selected from among the remaining frame images Pn. That is, in this case, though the frame image Pn having the smallest difference ΔSn is the frame image P4 as shown in FIG. 5B, since the frame image P4 is excluded from the target of the standard image processing condition determination processing as described above, the frame image Pn having the smallest difference ΔSn among the remaining frame images Pn is the frame image P1.

Thus, the standard image processing condition determination section 10 may determine the image processing condition, that is, the G value and the S value in the frame image P1 which was selected in such a way as the standard image processing condition $G_{st}$ and $S_{st}$ which is a standard. In the case shown in FIG. 4, the image processing condition, that is, the G value and the S value in the frame image P is finally determined as the standard image processing condition $G_{st}$ and $S_{st}$ which is a standard also in this case.

In the example shown in FIG. 4, both of the frame image Pn which was selected on the basis of the expression (6) as described above and the frame image Pn which was selected as described above are the frame image P1. However, the frame images Pn which are selected in the above cases are not necessarily the same frame image Pn.

[Image Processing]

The image processing section 10 performs image processing by applying the standard image processing condition $G_{st}$ and $S_{st}$ which was determined by the standard image processing condition determination section 10 as described above to each of the frame images Pn.

That is, in the embodiment, the image processing section 10 does not perform image processing by applying the G value and the S value which were calculated for each of the frame images Pn by the image processing condition calculation section 10 to each of the frame images Pn. The image processing section 10 performs image processing by uniformly applying the standard image processing condition $G_{st}$ and $S_{st}$ which was determined by the standard image processing condition determination section 10 (that is, the image processing condition in the one frame image Pn which was selected from among the plurality of frame images Pn (that is, the G value and the S value of the frame image P1 in the above example)) to each of the frame images Pn.

Also in this case, the image processing section 10 may perform image processing by uniformly applying the standard image processing condition $G_{st}$ and $S_{st}$ which was determined by the standard image processing condition determination section 10 to all the frame images Pn forming the moving image. Alternatively, the image processing section 10 may perform image processing by uniformly applying the standard image processing condition $G_{st}$ and $S_{st}$ which was determined by the standard image processing condition determination section 10 to a plurality of frame images Pn which were selected from the moving image by the user such as a radiation technologist and a doctor, for example.

In the latter case, the target of the image processing may be the plurality of frame images Pn which were selected from the moving image by the user as the target for extracting the reference region R in the above-mentioned reference region extraction processing. Alternatively, as the target of the image processing, the user may newly select a plurality of frame images Pn from the moving image.

As described above, according to the radiation image processing device 1 in the embodiment, the image processing condition for one frame image Pn is determined from among the image processing conditions for the plurality of frame images Pn forming a moving image as the standard image processing condition, that is, as the most standard image processing condition. The determined standard image processing condition is uniformly applied to each of the frame images Pn to perform image processing.

Thus, it is possible to perform contrast adjustment of each of the frame images Pn on the basis of the common standard ($G_{st}$ and $S_{st}$ in the above example) in the image processing to each of the frame images Pn forming the moving image. Thus, it is possible to generate the moving image which enables the doctor to accurately grasp the shape, the movement, the density change and such like of the imaging site (for example, the lung regions r) by watching the moving image.

According to the radiation image processing device 1 in the embodiment, the variation in the contrast caused by the change in the image is not suppressed as described in the above Japanese Patent Application Laid-Open Publication No. 2011-5050. Thus, in the moving image for example, the density of the lung regions r increases when a patient who is a subject breathes in and the density of the lung regions r decreases when the patient breathes out. Thus, the user can intuitively grasp the change in the structure such as the lung regions r by watching the moving image, and the property of visual confirmation of the moving image can be improved.

The above embodiment was made for a case of selecting one frame image Pn from among the plurality of frame images Pn forming the moving image and determining the image processing condition of the selected from image Pn as the standard image processing condition as described above.

However, in the standard image processing condition determination, the standard image processing condition determination section 10 may determine the standard image processing condition by selecting an optimum value for each of the parameters (for example, the G value and the S value)

which are included in the image processing conditions of the frame images Pn, for example.

That is, in the above case of FIG. 4 for example, as mentioned above, the median value of the G value is 827 of the image No. 3 (frame image P3), and the median value of the S value is 1481 of the image No. 4 (frame image P4). Thus, in this case, the standard image processing condition may be determined by selecting the optimum value for each of the parameters, that is, by setting the G value to 827 and the S value to 1481.

Even in such a configuration, the determined standard image processing condition is the most standard image processing condition as the image processing condition for each of the frame images Pn forming the moving image. Thus, by uniformly applying the standard image processing condition to each of the frame images Pn to perform image processing, the beneficial effect similar to that of the above embodiment can be obtained.

Also in this case, it is possible to perform the above standard image processing condition determination processing by excluding the parameters (that is, the G value and the S value which are the outlier values in the above example) of the image processing conditions which are the outlier values from the target of the standard image processing condition determination processing and targeting the remaining parameters of the image processing conditions. By such a configuration, it is possible to determine more appropriate parameters as the parameters of the standard image processing condition.

It goes without saying that the present invention is not limited to the above embodiments and others, and modifications can be appropriately made within the scope of the present invention.

What is claimed is:

1. A radiation image processing device which performs image processing to a moving image that is obtained by emitting radiation to a subject, the radiation image processing device comprising a hardware processor that:
   extracts a reference region from each of a plurality of frame images which form the moving image;
   calculates an image processing condition of the reference region for each of the frame images from which the reference region is extracted;
   determines a standard image processing condition which is a standard based on the calculated image processing condition of each of the frame images; and
   performs image processing by applying the determined standard image processing condition to each of the frame images.

2. The radiation image processing device according to claim 1, wherein the hardware processor selects one frame image from among the plurality of frame images for which the image processing condition is calculated, and the hardware processor determines the image processing condition of the selected one frame image as the standard image processing condition.

3. The radiation image processing device according to claim 1, wherein the hardware processor determines the standard image processing condition by selecting an optimum value for one or more parameters which are included in the image processing condition of each of the frame images.

4. The radiation image processing device according to claim 1, wherein the hardware processor extracts the reference region from each of all of frame images which form the moving image or each of a plurality of frame images among all of the frame images.

5. The radiation image processing device according to claim 1, wherein the hardware processor performs the image processing by applying the determined standard image processing condition to all of frame images which form the moving image or a frame image among all of the frame images.

6. The radiation image processing device according to claim 1, wherein the image processing condition includes a window width and a window level in image normalization processing.

7. The radiation image processing device according to claim 1, wherein the moving image is a moving image which is obtained by capturing a thorax that includes a lung region of the subject.

8. The radiation image processing device according to claim 1, wherein the hardware processor determines the standard image processing condition based on a median value of a parameter included in the image processing condition of the frame images.

* * * * *